(12) United States Patent
Dominick et al.

(10) Patent No.: US 11,177,031 B2
(45) Date of Patent: Nov. 16, 2021

(54) HEALTHCARE NETWORK

(71) Applicant: Siemens Healthcare GmbH, Erlangen (DE)

(72) Inventors: Lutz Dominick, Eggolsheim (DE); Vladyslav Ukis, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 189 days.

(21) Appl. No.: 16/128,679

(22) Filed: Sep. 12, 2018

(65) Prior Publication Data

US 2019/0088358 A1 Mar. 21, 2019

(30) Foreign Application Priority Data

Sep. 19, 2017 (EP) .................................. 171918550

(51) Int. Cl.
*G16H 30/20* (2018.01)
*G06F 21/62* (2013.01)
*G06F 16/51* (2019.01)
*G16H 10/60* (2018.01)
*G16H 40/20* (2018.01)

(52) U.S. Cl.
CPC ............. *G16H 30/20* (2018.01); *G06F 16/51* (2019.01); *G06F 21/6218* (2013.01); *G16H 10/60* (2018.01); *G16H 40/20* (2018.01)

(58) Field of Classification Search
CPC ........ G16H 10/20; G16H 10/60; G16H 40/20; G16H 30/20
USPC .......................................................... 705/3
See application file for complete search history.

(56) References Cited

U.S. PATENT DOCUMENTS

| 2006/0026205 | A1* | 2/2006 | Butterfield ............. G16H 40/63 |
| 2009/0036750 | A1 | 2/2009 | Weinstein et al. |
| 2009/0177249 | A1* | 7/2009 | Roberts .................. G16H 40/40 |
| | | | 607/60 |

(Continued)

FOREIGN PATENT DOCUMENTS

WO WO-2015164776 A1 * 10/2015 ............. G16H 70/00

OTHER PUBLICATIONS

European Office Action dated Dec. 3, 2019.

(Continued)

*Primary Examiner* — Hiep V Nguyen
(74) *Attorney, Agent, or Firm* — Harness, Dickey & Pierce, P.L.C.

(57) ABSTRACT

A computer-implemented system to facilitate access to a plurality of automated applications via a healthcare network including a plurality of devices The system is configured to maintain a first association between each of the plurality of automated applications and at least one defined input; and for each of the at least one defined input, a second association between the predefined input and a corresponding action. Responsive to receipt of a first defined input from a first device, the system identifies, based on the first association, at least one automated application. Further, the system triggers, based on the second association, at least one of the identified automated application to perform the action corresponding to the first defined input in order to process medical information associated with the first defined input; and causes at least one of the identified automated application to communicate information relating to the action to the first device.

23 Claims, 7 Drawing Sheets

(56) References Cited

U.S. PATENT DOCUMENTS

| | | |
|---|---|---|
| 2012/0215799 A1 | 8/2012 | Bohner et al. |
| 2014/0278536 A1 | 9/2014 | Zhang et al. |
| 2015/0363562 A1 | 12/2015 | Hallwachs |
| 2016/0019294 A1 | 1/2016 | Dong et al. |
| 2016/0283665 A1 | 9/2016 | Sampath et al. |

OTHER PUBLICATIONS

Extended European Search Report #17191855.0 dated Mar. 28, 2018.
Summons to Attend Oral Proceedings dated Oct. 12, 2020 in corresponding European Appln. No. 17191855.1.

* cited by examiner

| AA | Predefined input | Action |
|---|---|---|
| AA 151 | Predefined input 1 | Action 1 |
| | Predefined input 2 | Action 2 |
| | Predefined input 3 | Action 3 |
| AA 152 | Predefined input 1 | Action 4 |
| | Predefined input 4 | Action 5 |
| | Predefined input 5 | Action 6 |

FIG 3

HEALTHCARE NETWORK

PRIORITY STATEMENT

The present application hereby claims priority under 35 U.S.C. § 119 to European patent application number EP17191855.0 filed Sep. 19, 2017, the entire contents of which are hereby incorporated herein by reference.

FIELD

Embodiments of the present invention generally relate to, but not exclusively to, computer-implemented systems, methods and computer programs usable in facilitating access to automated applications via a healthcare network.

BACKGROUND

A healthcare network comprises a plurality of systems including devices, platforms and applications (also referred to as programs or computer programs). The devices may include medical devices (e.g. a picture archiving and communication system (PACS) and an ultrasound system), user terminals for use by medical professionals and patients, specialist user terminals (e.g. nurse call system), servers and medical data stores. The platforms facilitate the devices and applications to access services and repositories internal or external to the healthcare network. Applications operate on, or in conjunction with or accessible via the devices, and may include communication applications that facilitate communication between devices on the healthcare network, medical applications configured to process medical information, applications configured to manage patent information, applications for managing knowledge in a healthcare environment, applications configured to manage medical records.

Typically, a healthcare network comprises a mix of disparate proprietary and off-the-shelf systems, which are rarely integrated so as to operate homogeneously. Conventionally, proprietary systems were integrated by way of customized interfaces or customized workflows (e.g. System Analysis and Program Development (SAP) or Radiology Information System (RIS)) that tightly integrate the relevant medical systems. Some vendors do provide proprietary environments for integrating their proprietary systems, but these are vendor-specific and are usually incompatible with systems provided by other vendors. The health industry standards do not mandate all operational aspects required for fully integrating medical systems. In addition, there is very little guidance in the standards regarding integration of medical systems incorporating new technologies and/or involving multiple vendors. This being the case, interaction between disparate systems often requires manual intervention, which is undesirable.

Interaction between medical systems has also been enabled by way of customized automated applications (commonly referred to as medical robots or MediBOTs). The customized automated application comprises a user interface or a web service that interacts with users in a conversational format, and provides inputs to the relevant medical system that it is integrated with based on the interaction. Therefore, customized automated applications enable integration by patching individual medical systems, in which the patch is often provided by the vendor associated with the medical systems being patched. However, this type of patching leads to a non-homogeneous environment in which select medical systems are bridged together based on the healthcare organization's needs of that moment.

It is desirable to provide a homogeneous healthcare environment in which disparate medical systems can seamlessly operate.

SUMMARY

In a first embodiment, there is provided a computer-implemented system A computer-implemented system operable to facilitate access to a plurality of automated applications via a healthcare network, the healthcare network including a plurality of devices configured to process medical information, the system including one or more processors configured to:

maintain, in a database:
a first association between each of the plurality of automated applications and at least one predefined input, and
for each of the at least one predefined input, a second association between the predefined input and a corresponding action, wherein, in response to receiving the predefined input, at least one of the plurality of automated applications associated with the received predefined input includes program code configured to cause the at least one of the plurality of automated applications to perform the corresponding action in order to process medical information associated with the received predefined input;
in response to receiving a first predefined input of the at least one predefined input from a first device of the plurality of devices, identify, based on the first association, at least one automated application from the plurality of automated applications;
based on the second association, trigger at least one of the identified automated application to perform the action corresponding to the first predefined input in order to process medical information associated with the first predefined input; and
cause at least one of the identified automated application to communicate information relating to the action to the first device.

In a second embodiment, there is provided a method of facilitating access to a plurality of automated applications via a healthcare network, the healthcare network comprising a plurality of devices configured to process medical information, the method comprising:

maintaining, in a database:
a first association between each of the plurality of automated applications and at least one predefined input; and
for each of the at least one predefined input, a second association between the predefined input and a corresponding action, wherein, in response to receiving the predefined input, at least one of the plurality of automated applications associated with the received predefined input includes program code configured to cause the at least one of the plurality of automated applications to perform the corresponding action in order to process medical information associated with the received predefined input;
in response to receiving a first predefined input of the at least one predefined input from a first device of the plurality of devices, identifying, based on the first association, at least one automated application from the plurality of automated applications;
based on the second association, triggering at least one of the identified automated application to perform the action corresponding to the first predefined input in order to process medical information associated with the first predefined input; and causing at least one of the identified automated application to communicate information relating to the action to the first device.

In a third embodiment, there is provided a computer program stored in a memory or other nontransitory computer readable medium, comprising a set of instructions, which, when executed by a computerized device, cause the computerized device to perform a method of facilitating access to a plurality of automated applications via a healthcare network, the healthcare network comprising a plurality of devices configured to process medical information, the method comprising, at the computerized device:

maintaining, in a database:

a first association between each of the plurality of automated applications and at least one predefined input; and for each of the at least one predefined input, a second association between the predefined input and a corresponding action, wherein, in response to receiving the predefined input, at least one of the plurality of automated applications associated with the received predefined input includes program code configured to cause the at least one of the plurality of automated applications to perform the corresponding action in order to process medical information associated with the received predefined input;

in response to receiving a first predefined input of the at least one predefined input from a first device of the plurality of devices, identifying, based on the first association, at least one automated application from the plurality of automated applications;

based on the second association, triggering at least one of the identified automated application to perform the action corresponding to the first predefined input in order to process medical information associated with the first predefined input; and causing at least one of the identified automated application to communicate information relating to the action to the first device.

In a fourth embodiment, there is provided a computer-implemented system operable to facilitate access to a plurality of automated applications via a healthcare network, the healthcare network comprising a plurality of devices configured to process medical information, wherein, each of the plurality of automated applications is configured to be triggered in response to a predefined input associated therewith from a device from the plurality of devices and includes program code configured to process medical information associated with the received predefined input, the system being configured to:

maintain, in a database, an association between a first of the plurality of automated applications and at least one, different, of the plurality of automated applications;

in response to receiving a predefined input associated with the first automated application from a first device of the plurality of devices, trigger the first automated application to process medical information associated with the predefined input; and cause the first automated application to trigger the at least one of the plurality of automated applications and communicate information relating to the medical information processed thereby.

Further features and advantages of the invention will become apparent from the following description of embodiments, given by way of example only, which is made with reference to the accompanying drawings.

BRIEF DESCRIPTION OF THE DRAWINGS

FIG. 3 shows a table depicting an example of entries in a database in accordance with embodiments;

DETAILED DESCRIPTION OF THE EXAMPLE EMBODIMENTS

Figure 1:
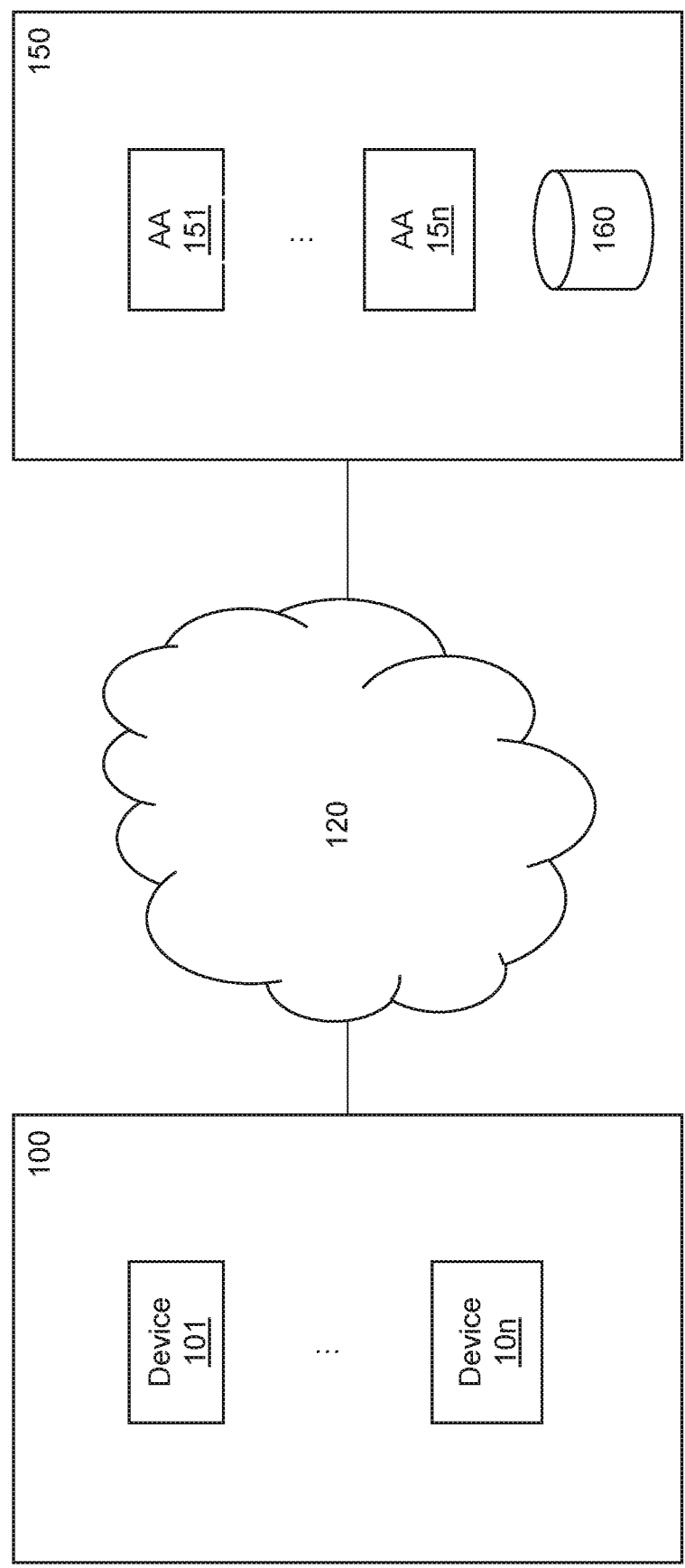
FIG. 1 shows a schematic block diagram of an example of a healthcare network in accordance with embodiments.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing"

or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Referring to FIG. 1, there is shown schematically an example of a healthcare infrastructure. The healthcare infrastructure comprises a number of systems. The term "system" is used herein to denote an entity (or entities) in the healthcare infrastructure. A system may be embodied in the form of apparatus, hardware, software, a function, a virtualized resource, etc., or any combination of same.

The healthcare infrastructure comprises a healthcare network 100, which in turn comprises a plurality of systems including devices 101-10n, platforms (not shown) and applications (not shown). A healthcare network can comprise at least some different and/or additional components to those shown in FIG. 1.

The devices 101-10n, which may be operable by at least one user, such as a healthcare professional or a patient, are configured to process medical information. The devices 101-10n may comprise a user terminal (for example, a telephone, a mobile telephone, a tablet computer and a personal computer), a server configured to provision applications and data to the devices 101-10n, a data store configured to store medical information, a specialist user terminal (for example, a nurse call system) and a medical device (for example, a picture archiving and communication system (PACS) and an ultrasound system). At least some of the devices 101-10n may be communicatively coupled to each other via, for example, a local area network, metropolitan area network or a wide area network, and may have access to systems external to the healthcare network 100 via a Candidate Access Network (CAN) 120. The devices 101-10n may comprise one or more processors (not shown) for performing various data processing operations according to embodiments and/or one or more memories (not shown) for storing various data according to embodiments.

The CAN 120 may, for example, be a wireless access network or a wired access network. Examples of wireless access networks include, but are not limited to Wireless Local Area Networks (WLANs) and mobile radio access networks. An example of a mobile radio access network is an Evolved Universal Terrestrial Radio Access Network (E-UTRAN). An example of a wired access network is an Asymmetric Digital Subscriber Line (ADSL).

At least some of the devices 101-10n have access to a computer-implemented system 150. In this example, the computer-implemented system 150 comprises a plurality of Automated Applications (AA) 151-15n for access by the devices 101-10n. The computer-implemented system 150 may be implemented on a single computer or a network of computers that are accessible by the devices 101-10n via the CAN 120. In examples, the computer-implemented system 150 may be a central or location-specific distributed system. The computer-implemented system 150 comprises one or more processors (not shown) for performing various data processing operations according to embodiments. The computer-implemented system 150 comprises or otherwise have access to a database 160 for storing various data according to embodiments. The database may comprise one or more memories (not shown) and may be integral to or external to the computer-implemented system 150. The database may comprise memory within the computer-implemented system 150 (not shown) which is available for storing data regarding provisioning of the AAs 151-15n. The memory may be volatile so that data stored therein may need to be re-learnt upon failure/re-boot of the computer-implemented system 150. A computer-implemented system can comprise at least some different and/or additional components to those shown in FIG. 1.

Each of the AAs 151-15n (also referred to as medical robots or mediBOTS) act as a service accessible by the devices 101-10n. For example, the AAs 151-15n may include a dosage service that determines dosage to be administered based on a patient's medical condition, or a scanner protocol service that identifies the right protocol for scanner usage to ensure correct diagnosis of a medical condition.

Figure 2:
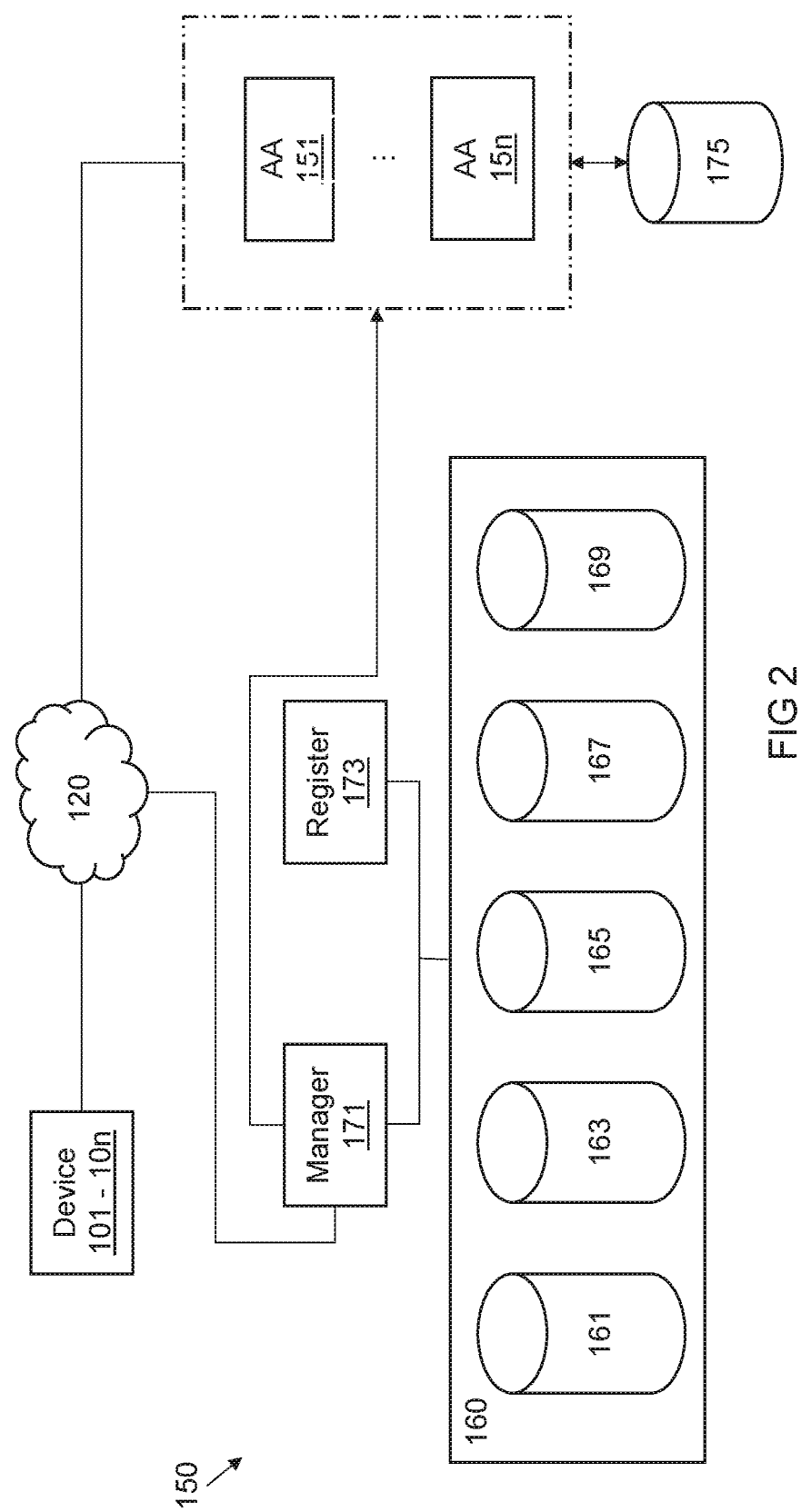
FIG. 2 shows a schematic block diagram of an example of a healthcare network in accordance with embodiments.

Referring to FIG. 2, there is shown an example of facilitating access to the AAs 151-15n to the devices 101-10n. This example is performed in the healthcare infrastructure described above with reference to FIG. 1.

In this example, the computer-implemented system 150 comprises a manager system 171 that interacts with the devices 101-10n over one or more communication channels via the CAN 120, whereby to facilitate access to the AAs 151-15n. The computer-implemented system 150 additionally comprises a register system 173 that maintains various associations in relation to the AAs 151-15n. The manager system 171 and the register system 173 have access to a database 160 for facilitating access to the AAs 151-15n. The computer-implemented system 150 may optionally comprise a data store 175 for storing medical information, and for use by the AAs 151-15n when processing medical information. The database 160 and the data store 175 may be maintained on the same physical entity or on separate physical entities.

The register system 173 maintains, in a portion 161 of the database 160, a first association between each of the AAs 151-15n and at least one predefined input. The predefined input may be a question, for example "can this medication be administered to patient with high blood pressure?", or data indicative of an impulse from a medical device, for example data indicative of a blood pressure, or a user device. The impulse may, for example, be electrical, mechanical, magnetic or electromagnetic.

For each of the at least one predefined input, the register system 173 maintains, in a portion 163 of the database 160, a second association between the predefined input and a corresponding action. In response to receiving one of the predefined inputs, at least one of the AAs 151-15n associated with the received predefined input includes program code configured to cause the relevant of the AAs 151-15n to perform the action corresponding to the received predefined input in order to process medical information associated therewith. For example, in response to receiving an input indicative of emergency situation involving dosage regimen of a medicine, a dosage service may respond to the received input and process the medical information in order to suggest changes to the dosage regimen.

The first and second associations therefore identify inputs that cause an AA from the AAs 151-15n to be triggered to perform an action corresponding to the received input. An example of entries in the database 160 defining the first and second associations is shown with reference to FIG. 3. In this example, AA 151 is associated with predefined inputs 1-3, which in turn are associated with corresponding actions 1-3. AA 152 is associated with predefined inputs 1, 4 and 5, which in turn are associated with corresponding actions 4-6.

It will be noted that AAs 151 and 152 are both associated with the predefined input 1, but these inputs are associated with different actions.

In response to receiving a first predefined input of the predefined inputs from device 101 of the devices 101-10n, the manager system 171 identifies, based on the first association, at least one AA from the AAs 151-15n (hereinafter referred to as identified AA(s)). Based on the second association, the manager system 171 triggers at least one of the identified AA(s) to perform the action corresponding to the first predefined input in order to process medical information associated with the first predefined input. The manager system 171 also causes at least one of the identified AA(s) to communicate information relating to the action to the device 101.

For example, in response to receiving an input regarding protocols for efficient operation of a PACS device therefrom, the manager system 171 may identify a PACS protocol service that is associated with the received input. In this example, in response to identifying the PACS protocol service based on the first association, the computer-implemented system 150 triggers the PACS protocol service in order to cause it to process medical information whereby to identify a protocol for efficient operation of the PACS device and cause the PACS protocol service to communicate information regarding the identified protocol to the PACS device.

Therefore, the framework enables medical systems to be flexibly integrated in the healthcare infrastructure. The framework is based on predefined inputs associated with the AAs 151-15n and actions performed by the AAs 151-15n in response to the predefined inputs, and as a consequence is independent of system-level customisations that were conventionally performed to integrate selected medical systems. Thus, the framework enables a homogeneous environment in which systems can be flexibly integrated.

In the example set out with reference to FIG. 3, in response to receiving predefined input 1 from device 101 of the devices 101-10n, the manager system 171 identifies, based on the first association, that AAs 151 and 152 are associated with the predefined input 1. In this case, the manager system 171 may selectively trigger one of the AAs 151 or 152 based on, for example, one or more further associations discussed herein below, or may trigger both of the AAs 151 and 152 to process medical information associated with the predefined input 1. In the event that both the AAs 151 and 152 are triggered, the manager system 171 may cause the AAs 151 and 152 to either individually communicate information relating to their corresponding action to the device 101, or may cause them to collaborate when performing their corresponding actions and communicate information based on the collaboration to the device 101.

In examples, a predefined input may be received from one of the devices 101-10n associated with a room in the healthcare infrastructure, such as an operation theatre, or a healthcare professional in such a room. In this case, the location of the device defines the context associated with the predefined input, and the manager system 171 may identify at least one of the AAs 151-15n based in part on the combination of the first association and the context associated with the received predefined input. Context may be based on one or more additional or alternative factors, such as intended purpose.

With continued reference to FIG. 2, the manager system 171 is associated with one or more communication channels for receiving the predefined inputs from the devices 101-10n. The communication channels may in turn be associated to one or more interfaces for interacting via an application layer of the devices 101-10n. The interface may be a conversational interface for receiving the predefined input from a user operating the device 101-10n and be configured to receive the predefined input as part of a natural language conversation. The interface may alternatively or additionally be a non-conversational interface. Examples of conversational interfaces include media communication applications, such as Skype™, email applications, social media applications, such as Twitter™, messaging applications, such as WatsApp™, or a custom application, such as EMIS™ GP Data Viewer. An example of a non-conversational interface is an interface with drop down menus. The register system 173 may maintain, in a portion 165 of the database 160, a third association between the AAs 151-15n and at least one communication channel, and subsequently use the third association in addition to the first addition when identifying the identified AA(s).

In this case, the manager system 173 may identify the identified AA(s) associated with a received predefined input based at least in part on the first association and the third association. For example, in response to receiving a predefined input via a communication channel associated with a conversation interface, the manager system 171 determines which of the AAs 151-15n are associated with the communication channel based on the third association and from those of the AAs 151-15n identify one or more AAs that are associated with the predefined input based on the first association.

In embodiments, in response to receiving data identifying a further AA, different from the AAs 151-15n, the register system 173 registers, in the portion 161 of the database 160, the first association between the further AA and one or more of the predefined inputs. For each of the predefined inputs associated with the further AA, the register system 173 registers, in the portion 163 of the database 160, the second association between the predefined input and a corresponding action. By maintaining the first and the second association in respect of the further AA, the register system 173 facilitates access thereto via the devices 101-10n.

Therefore, the framework enables new AAs to be made available to the devices 101-10n. In examples, the new AAs may add features to conventional medical systems, enhance user interface of a medical system by providing a conversational interface and integrate medical systems. Thus, the register system 173 enables the healthcare infrastructure to flexibly introduce newer AAs in accordance with the current requirements of the healthcare infrastructure. Newer AAs may enhance the capabilities within the healthcare infrastructure by being responsive to newer predefined inputs, and/or processing medical information based on newer actions, which may, for example, be a result of a recently concluded research.

In embodiments, the register system 173 removes, from the portion 161 of the database 160, the first association between AA 151 of the AAs 151-15n and each of the predefined inputs associated therewith, thereby preventing access to the AA 151 via the healthcare network 100. By removing the first association in respect of the AA 151, the register system 173 prevents the AA 151 from being identified in response to any of the predefined inputs and as a consequence prevents the AA 151 from being triggered. Thus, the register system 173 efficiently prevents access to an AA that may, for example, not be compatible with the current requirements of the healthcare infrastructure.

In embodiments, the register system 173 maintains, in a portion 167 of the database 160, a fourth association between an action associated with at least one of the AAs 151-15n and one or more of the AAs 151-15n, and in response to performing the action corresponding to a predefined input, the manager system 171 causes, based on the fourth association, the identified AA(s), subsequent to performing the action corresponding to the received predefined input, to communicate information relating to the action to the associated one or more of the AAs 151-15n, thereby causing the associated one or more of the AAs to process information associated with the action. For example, an action of administering an emergency dose of a medicine by a dosage service, may be associated with an emergency care monitor service, and in this case when the dosage service causes an emergency dose of a medicine to be administered, the dosage service informs the emergency care monitor service to act on the input, i.e. administering of the emergency dose of the medicine, and take appropriate next action based on this input. Therefore, the framework enables integration between medical systems by linking inputs and actions.

In embodiments, each of the aforementioned users are associated with a privilege parameter based at least in part on a user role, such as doctor, and/or a user identity, such as a name. In this case, the register system 173 maintains, in a portion 169 of the database 160, a fifth association between at least one of the AAs 151-15n and at least one of the users based at least in part on the privilege parameter associated therewith. In this case, the manager system 171 identifies one or more AAs from the AAs 151-15n based at least in part on the combination of the aforementioned first association and the fifth association. Therefore, the user is allowed to access the AAs 151-15n on the basis of the privileges accorded thereto. For example, access to an emergency care monitor service may be restricted to healthcare professionals on duty at the time in an emergency ward.

In response to receiving data indicative of a change to the privilege parameter associated with a user of the plurality of users, the register system 173 may update the fifth association corresponding to the user based at least in part on the data indicative of the change. For example, upon change of doctor on duty in an emergency ward, the register system 173 may be notified and it updates the fifth association accordingly. Therefore, the user is allowed access to the relevant AAs based on a context associated therewith.

In some embodiments, at least one of the users is associated with a customisation parameter based at least in part on user preference and/or a user setting. The user preference and/or user settings may, for example, comprise data indicative of a user's preference between AAs. In this case, the register system 173 maintains the fifth association corresponding to relevant users based at least in part on their associated customisation parameter. Therefore, individual user's preferences and/or settings are taken into account when identifying AAs in response to a predefined input from a device associated therewith.

In at least some embodiments, in response to receiving data indicative of a change to the customisation parameter associated with a user of the plurality of users, the register system 173 updates the fifth association corresponding to the user based on at least in part on the data indicative of the change. For example, a user previously preferred a first dosage service but has now changed their preference to a second dosage service. Therefore, change in user configuration is taken into account, and the relevant AAs from the AAs 151-15n are identified accordingly.

In embodiments, the register system 173 maintains, in a portion 169 of the database 160, a sixth association between an action corresponding to one of the predefined inputs and at least one of the users. In this case, in response to performing an action corresponding to a received predefined input, the manager system 171 causes, based on the sixth association, the identified AA(s) to communicate information relating to the action to the associated users. For example, an emergency action of a dosage service may be associated with each of the healthcare professionals on duty in an emergency ward, and accordingly when an emergency action is performed by the dosage service all of the healthcare professionals on duty will be informed so that they are able to monitor and manage the emergency situation.

In embodiments, the register system 173 maintains, in the portion 169 of the database 160, a seventh association between an action corresponding to at least one of the predefined inputs with at least one of the devices 101-10n. In this case, in response to performing an action corresponding to a received predefined input, the manager system 171 causes, based on the seventh association, the identified AA(s) to communicate information relating to the action to the associated devices. For example, in response to administering an emergency dosage of a medicine to a patient, the manager system 171 causes the dosage service to communicate information relating to this action to the devices associated with healthcare professionals on duty in an emergency ward.

In embodiments, the register system 173 maintains, in a portion (not shown) of the database 160, an eighth association between at least of the AAs 151-15n and a program (also referred to as a computer program) operable on at least one of the devices 101-10n. In this case, in response to receiving a predefined input, the manager system 171 causes the identified AA(s) to operate in conjunction with the associated program in order to process medical information associated with the received predefined input. For example, a dosage service may be caused to operate in conjunction with a dosage program in order to determine a dosage of a medicine that should be administered to a patient. Therefore, embodiments enable new features and/or newer processing capabilities to coexist with conventional systems.

In at least some embodiments, each of the predefined inputs correspond to an input from a medical domain, and/or each of the actions corresponding to the at least one predefined inputs correspond to an action from a medical domain.

Figure 4:
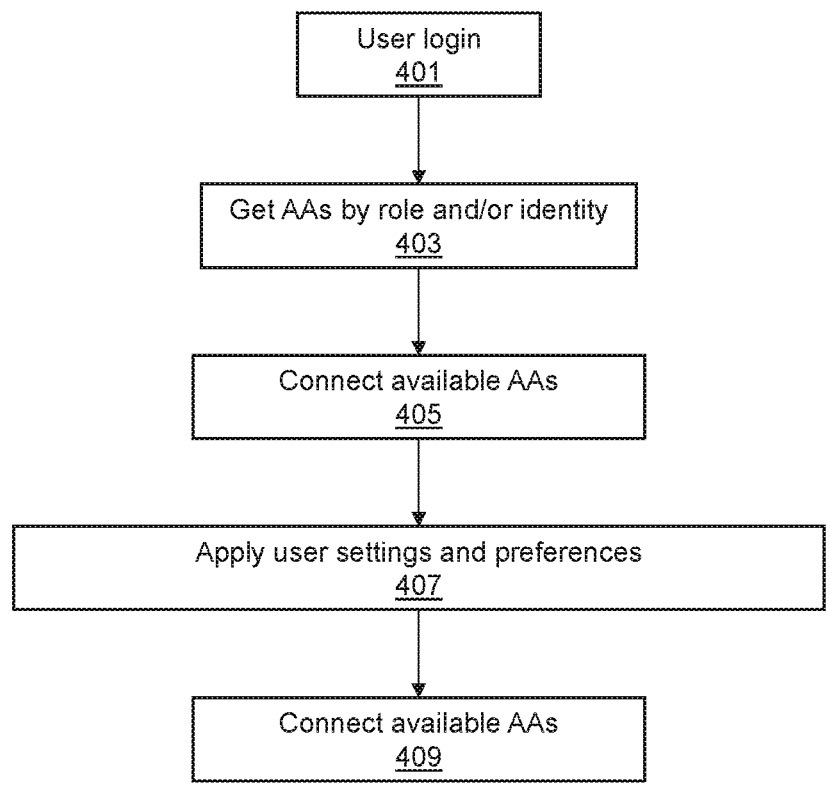
FIG. 4 shows a flow diagram depicting an example of processing data in accordance with embodiments.

Referring to FIG. 4, there is shown an example of a user-specific environment for interaction with the computer-implemented system 150 in accordance with embodiments. This could be used, for example, when a user registers or logs in with the healthcare infrastructure. The example may be performed in the healthcare infrastructure described above with reference to FIGS. 1 and 2.

At block 401, a user logs in on device 101 of the devices 101-10n. In response to the user login, the manager system 171 prepares a list of AA(s) based at least in part on the aforementioned fifth association indicative of the privilege parameter associated with the user (block 403). AA(s) may be added and/or removed from the prepared list of AA(s) based at least in part on the aforementioned customization parameter associated with the user. The manager system 171 may display the prepared list via a display associated with the device 101. The manager system 171 then identifies one or more communication channels associated with the AA(s) in the prepared list, and establishes a communication session with the device 101 and connects thereto via one or more of the identified communication channels (block 405). The manager system 171 may additionally apply user settings and preferences in respect of the AAs 151-15n in the prepared list (block 407), and thereafter connect the AAs 151-15n in the prepared list in order to be able to receive one or more of the predefined inputs from the user via the device 101 (block 409). For example, the user may be interacting via a conversational interface and during the course of the interaction send one of the predefined inputs, which causes the manager system 171 to identify relevant AA(s) from the prepared list to perform an action corresponding the predefined input in order to process medical information. The list of AA(s) is user-specific, and is generated in response to login so is up to date. Therefore, the user is enabled to have visibility of the AAs accessible to them, and trigger them when interacting with their device as a matter of course.

Figure 5:
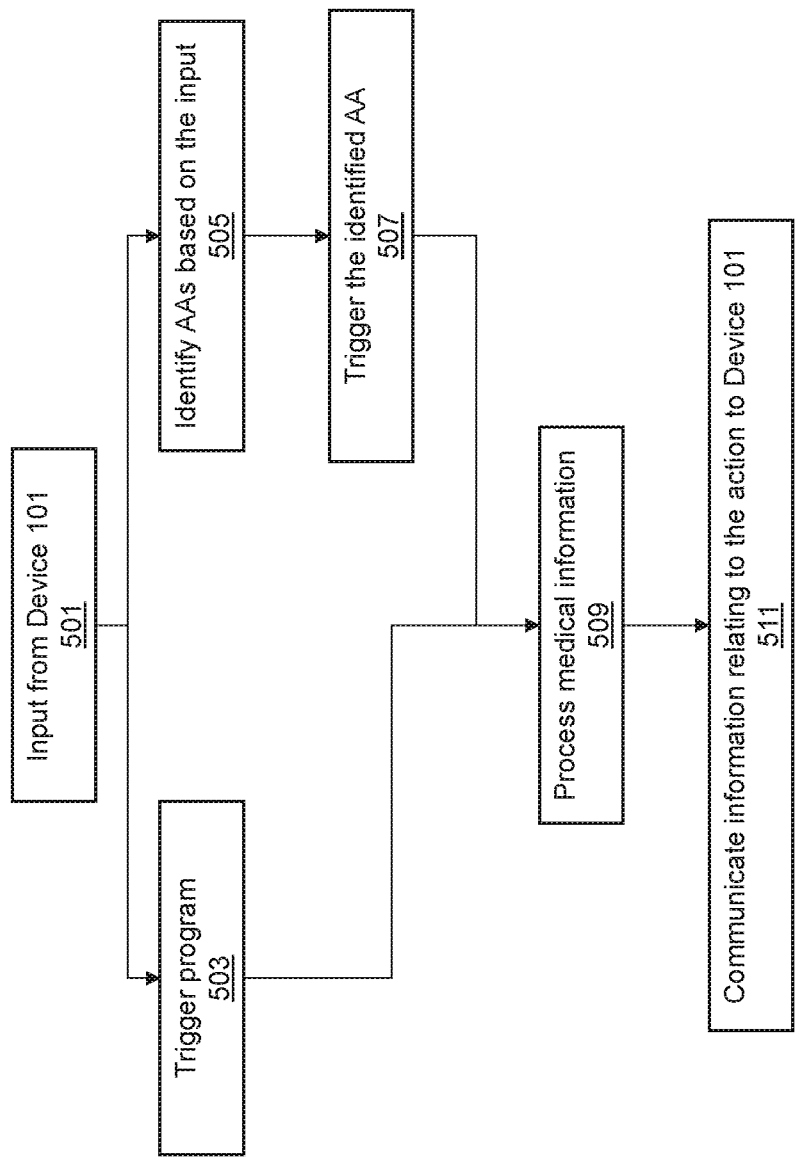
FIG. 5 shows a flow diagram depicting an example of processing data in accordance with embodiments.

Referring to FIG. 5, there is shown an example of an AA collaborating with a program in order to process medical information associated with a received predefined input in accordance with embodiments. This could be used, for example, when an AA is required to operate in conjunction with a program in order to process medical information. The example may be performed in the healthcare infrastructure described above with reference to FIGS. 1 and 2.

At block 501, one of the predefined inputs is received from device 101 of the devices 101-10n. The received predefined input causes a program, maintained locally on the device or otherwise accessible by the device 101, to be triggered (block 503). Separately, in response to receiving the predefined input, the manager system 171 identifies at least one of the AAs 151-15n based on the aforementioned first association (block 505). The manager system 171 triggers the identified AA(s) to perform an action corresponding to the received predefined input (block 507). Based on the aforementioned eighth association, the manager system 171 causes the identified AA(s) to operate in conjunction with the program on the device 101 to process medical information associated with the predefined input (block 509), and communicate information relating to the action to the device 101 (block 511).

Figure 6:
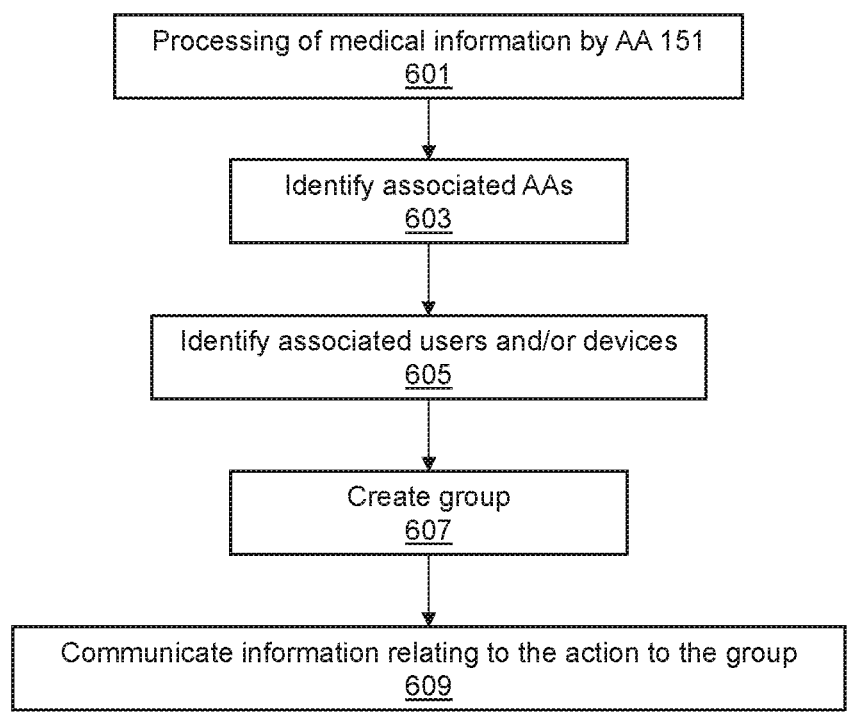
FIG. 6 shows a flow diagram depicting an example of processing data in accordance with embodiments.

Referring to FIG. 6, there is shown an example of creating groups comprising users, devices and AAs that are associated with an action performed by an AA in accordance with embodiments. This could be used, for example, when information relating to an action performed by an AA is to be disseminated to a wider group. The example may be performed in the healthcare infrastructure described above with reference to FIGS. 1 and 2.

In this example, in response to one of the predefined inputs, the manager system 171 triggers AA 151 to process medical information associated with the received predefined input (block 601). The manager system 171 identifies, based on the aforementioned fourth association, one or more of the AAs 151-15n associated with the AA 151 (block 603). The manager system 171 also identifies one or more of the users, based on the aforementioned sixth association, and/or one or more of the devices 101-10n, based on the aforementioned seventh association, associated with the action corresponding to the received predefined input associated with the AA 151 (block 609). The manager system 171 creates a group comprising the AA(s), user(s) and device(s) associated to the action corresponding to the received predefined input associated with the AA 151 (block 607), and cause the AA 151 to communicate information relating to the action to the members of the group (block 609).

In at least some of the embodiments, the register system 173 maintains one or more groups based on the fourth association, the sixth association and/or the seventh association. In this case, the manager system 171 causes the identified AA(s) to communicate information relating to the action performed to each of the users, the devices and the AAs in the group. For example, in response to an emergency action performed by an AA, the manager system 171 causes the AA to communicate information relating to the action to the healthcare professionals, devices and AAs in an emergency response group. In examples, the manager system 171 may allow users and devices in a group to collaborate, and monitor their interaction for further predefined input(s).

Figure 7:
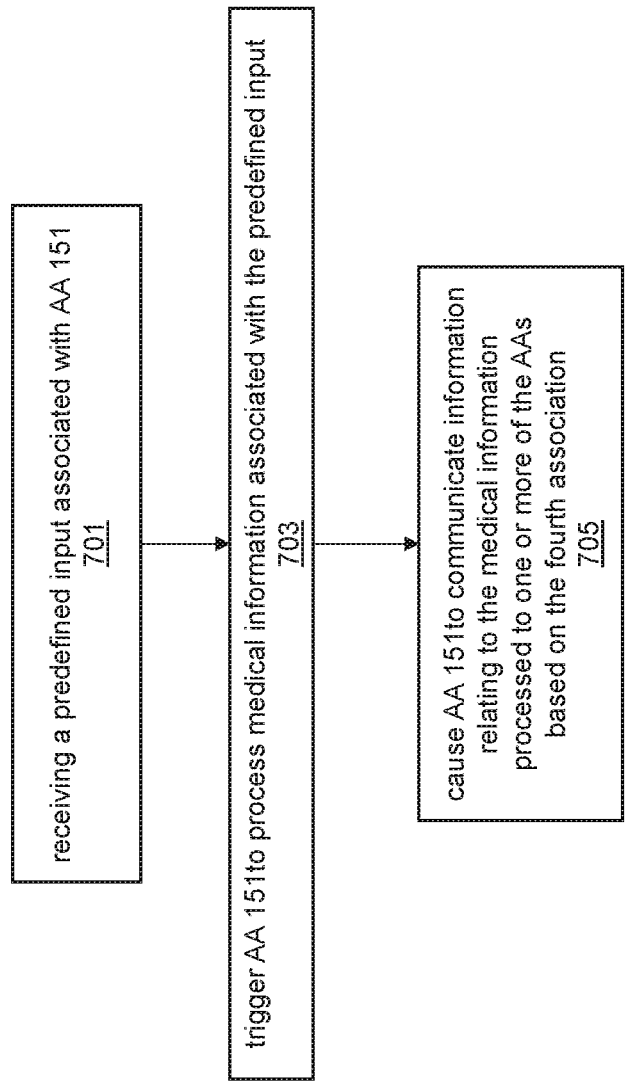
FIG. 7 shows a flow diagram depicting an example of processing data in accordance with embodiments.

Referring to FIG. 7, there is shown an example of an action of an AA causing further AAs to be triggered in accordance with embodiments. This could be used, for example, when information relating to an action performed by an AA is required to trigger further AAs. The example may be performed in the healthcare infrastructure described above with reference to FIGS. 1 and 2.

In this example, in response to receiving a predefined input associated with AA 151 from device 101 (block 701), based on the first association, the manager system 171 triggers the AA 151 to process medical information associated with the received predefined input (block 703). Based on the fourth association, the manager system 171 causes the AA 151 to trigger one or more of different of the AAs 151-15n associated therewith and communicate information relating to the processed medical information (block 705). In this case, the manager system 171 causes the identified AA(s) to trigger further AAs based on the action performed, and thereby causes a series of actions to be performed based on the outcome at each stage of processing. For example, a dosage service, when administering an emergency dosage of a medicine, be configured to trigger an emergency care monitor service, which then triggers further AAs depending on patient's reaction to the emergency dosage.

Therefore, the framework enables homogeneous environments in which interaction between medical systems and AA(s) is streamlined. Specifically, the embodiments manage various associations in order to trigger relevant AA(s) based on predefined inputs from the devices to process medical information and cause information relating to the actions performed to be communicated to the device, and optionally to further relevant AA(s), user(s) and/or device(s) based on associations. The embodiments enable access to AA(s) to be added and removed with ease. Therefore, the embodiments define an AA ontology based on associations.

The above are to be understood as illustrative examples. Further examples are envisaged.

In examples described above, the healthcare infrastructure comprises a healthcare network 100, one CAN 120 and one computer-implemented system 150. In other examples, the healthcare infrastructure comprises more than one CAN.

In examples described above, the computer-implemented system 150 comprises AAs 151-15n, one manager system 171, one database 160 and one register system 173. In other examples, the computer-implemented system 150 comprises additional systems.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented system operable to facilitate access to a plurality of customized automated applications via a healthcare network, the healthcare network including a plurality of devices configured to process medical information, the computer-implemented system including one or more processors configured to:
    maintain, in a database, using a register,
        a first association between each of the plurality of customized automated applications and at least one defined input, and
        for each of the at least one defined input, a second association between the at least one defined input and a corresponding first action, wherein, in response to receiving the at least one defined input, at least one of the plurality of customized automated applications associated with the at least one defined input received includes program code configured to cause the at least one of the plurality of customized automated applications to perform the corresponding first action in order to process medical information associated with the at least one defined input received;
    identify, using a manager, based on the first association, in response to receiving a first defined input of the at least one defined input from a first device of the plurality of devices, at least one customized automated application from the plurality of customized automated applications;
    trigger based on the second association, using the manager, at least one of the customized automated applications identified to perform the first action corresponding to the first defined input in order to process medical information associated with the first defined input;
    cause at least one of the at least one customized automated application identified to communicate information relating to the corresponding first action to the first device, using the manager;
    maintain, in the database, using the register, a third association between a second action associated with at least one of the plurality of customized automated applications and one or more of the plurality of customized automated applications; and
    cause based on the third association, using the manager, in response to performing the first action corresponding to the first defined input, the at least one of the customized automated applications identified to communicate information relating to the second action to the associated one or more of the plurality of customized automated applications via a communication channel defined by the third association.

2. The computer-implemented system of claim 1, wherein one or more processors of the computer-implemented system is configured to:
    register in the database, in response to receiving data identifying a further customized automated application, the further customized automated application being different from the plurality of customized automated applications, the registering including:
    registering the first association between the further customized automated application and one or more of the at least one defined input; and
    registering for each of the at least one defined input associated with the further customized automated application, the second association between the defined input and a corresponding first action, thereby facilitating access to the further customized automated application via the healthcare network.

3. The computer-implemented system of claim 2, wherein one or more processors of the computer-implemented system is configured to:
    remove, from the database, the first association between a first customized automated application of the plurality of customized automated applications and each defined input of the at least one defined associated therewith, thereby preventing access to the first customized automated application via the healthcare network.

4. The computer-implemented system of claim 2, wherein each input of the at least one defined input correspond to a respective input from a medical domain.

5. The computer-implemented system of claim 2, wherein each action, of the actions corresponding to the at least one defined input, corresponds to an action from a medical domain.

6. The computer-implemented system of claim 1, wherein one or more processors of the computer-implemented system is configured to:
    remove, from the database, the first association between a first customized automated application of the plurality of customized automated applications and each defined input of the at least one defined associated therewith, thereby preventing access to the first customized automated application via the healthcare network.

7. The computer-implemented system of claim 1, wherein at least some of the plurality of devices are operable by a plurality of users, each of the plurality of users being associated with a privilege parameter based at least in part on at least one of a user role and a user identity, wherein the one or more processors of the computer-implemented system is configured to:

maintain, in the database, using the register, a fourth association between at least one of the plurality of customized automated applications and at least one of the plurality of users, based at least in part on the privilege parameter associated with the at least one of the plurality of users; and perform identification based at least in part on a combination of the first association and the fourth association.

8. The computer-implemented system of claim 7, wherein the one or more processors of the computer-implemented system is configured to, in response to receiving data indicative of a first change to the privilege parameter associated with a first user of the plurality of users, update the fourth association corresponding to the first user based at least in part on the data received, indicative of the first change.

9. The computer-implemented system of claim 8, wherein at least one of the plurality of users is associated with a customization parameter based at least in part on at least one of a user preference and a user setting, wherein the one or more processors of the computer-implemented system is configured to maintain, using the register, the fourth association corresponding to the at least one of the plurality of users based at least in part on the customization parameter.

10. The computer-implemented system of claim 9, wherein the one or more processors of the computer-implemented system is configured to, in response to receiving data indicative of a second change to the customization parameter associated with a second user of the plurality of users, update the fourth association corresponding to the second user based on at least in part on the data received, indicative of the second change.

11. The computer-implemented system of claim 7, wherein at least one of the plurality of users is associated with a customization parameter based at least in part on at least one of a user preference and a user setting, wherein the one or more processors of the computer-implemented system is configured to maintain, using the register, the fourth association corresponding to the at least one of the plurality of users based at least in part on the customization parameter.

12. The computer-implemented system of claim 11, wherein the one or more processors of the computer-implemented system is configured to, in response to receiving data indicative of a second change to the customization parameter associated with a second user of the plurality of users, update the fourth association corresponding to the second user based on at least in part on the data received, indicative of the second change.

13. The computer-implemented system of claim 7, wherein the one or more processors of the computer-implemented system is configured to:

maintain, in the database, using the register, a fifth association between a third action corresponding to the at least one of the defined input associated with the at least one of the plurality of customized automated applications and at least one of the plurality of users; and cause based on the fifth association, using the manager, in response to performing the first action corresponding to the first defined input, the at least one of the customized automated applications identified to communicate information relating to the third action to the at least one of the plurality of users.

14. The computer-implemented system of claim 13, wherein the one or more processors of the computer-implemented system is configured to:

maintain, in the database, using the register, a sixth association between a fourth action corresponding to the at least one of the defined input associated with the at least one of the plurality of customized automated applications and at least one of the plurality of devices; and cause based on the sixth association, using the manager, in response to performing the first action corresponding to the first defined input, the at least one of the customized automated application identified to communicate information relating to the fourth action to the at least one of the plurality of devices.

15. The computer-implemented system of claim 7, wherein the one or more processors of the computer-implemented system is configured to:

maintain, in the database, using the register, a sixth association between a fourth action corresponding to the at least one of the defined input associated with the at least one of the plurality of customized automated applications and at least one of the plurality of devices; and cause based on the sixth association, using the manager, in response to performing the first action corresponding to the first defined input, the at least one of the customized automated application identified to communicate information relating to the fourth action to the at least one of the plurality of devices.

16. The computer-implemented system of claim 1, wherein the one or more processors of the computer-implemented system is configured to:

maintain, in the database, using the register, a sixth association between a fourth action corresponding to the at least one of the defined input associated with the at least one of the plurality of customized automated applications and at least one of the plurality of devices; and cause based on the sixth association, using the manager, in response to performing the first action corresponding to the first defined input, the at least one of the customized automated application identified to communicate information relating to the fourth action to the at least one of the plurality of devices.

17. The computer-implemented system of claim 1, wherein the one or more processors of the computer-implemented system is configured to:

maintain, in the database, using the register, a seventh association between at least one of the plurality of customized automated applications and a program operable on at least one of the plurality of devices; and perform, based on the seventh association, a fourth action to cause the at least one of the customized automated application identified to operate in conjunction with the program in order to process medical information associated with the first defined input, using the manager.

18. The computer-implemented system of claim 1, wherein each input of the at least one defined input correspond to a respective input from a medical domain.

19. The computer-implemented system of claim 1, wherein the first action corresponds to an action from a medical domain.

20. The computer-implemented system of claim 1, wherein the communication channel defined by the third association includes a plurality of communication channels for communicating over a given network connection.

21. A method of facilitating access to a plurality of customized automated applications via a healthcare network, the healthcare network comprising a plurality of devices configured to process medical information, the method comprising:

maintaining, in a database, using a register,
  a first association between each of the plurality of customized automated applications and at least one defined input, and
  for each of the at least one defined input, a second association between the at least one defined input and a corresponding first action, wherein, in response to receiving the at least one defined input, at least one of the plurality of customized automated applications associated with the at least one defined input received includes program code configured to cause the at least one of the plurality of customized automated applications to perform the corresponding first action in order to process medical information associated with the at least one defined input received;
identifying, using a manager, based on the first association, in response to receiving a first defined input of the at least one defined input from a first device of the plurality of devices, at least one customized automated application from the plurality of customized automated applications;
triggering based on the second association, using the manager, at least one of the customized automated application identified to perform the first action corresponding to the first defined input in order to process medical information associated with the first defined input;
causing at least one of the at least one customized automated application identified to communicate information relating to the corresponding first action to the first device;
maintaining, in the database, using the register, a third association between a second action associated with at least one of the plurality of customized automated applications and one or more of the plurality of customized automated applications; and
causing based on the third association, using the manager, in response to performing the first action corresponding to the first defined input, the at least one of the customized automated applications identified to communicate information relating to the second action to the associated one or more of the plurality of customized automated applications via a communication channel defined by the third association.

22. A non-transitory computer readable medium storing a computer program including a set of instructions, which, when executed by a computerized device, cause the computerized device to perform a method of facilitating access to a plurality of customized automated applications via a healthcare network, the healthcare network comprising a plurality of devices configured to process medical information, the method comprising, at the computerized device:
  maintaining, in a database, using a register,
    a first association between each of the plurality of customized automated applications and at least one defined input, and
    for each of the at least one defined input, a second association between the at least one defined input and a corresponding first action, wherein, in response to receiving the at least one defined input, at least one of the plurality of customized automated applications associated with the at least one defined input received includes program code configured to cause the at least one of the plurality of customized automated applications to perform the corresponding first action in order to process medical information associated with the at least one defined input received;
  identifying based on the first association, using a manager, in response to receiving a first defined input of the at least one defined input from a first device of the plurality of devices, at least one customized automated application from the plurality of customized automated applications;
  triggering based on the second association, using the manager, at least one of the customized automated application identified to perform the first action corresponding to the first defined input in order to process medical information associated with the first defined input;
  causing at least one of the at least one customized automated application identified to communicate information relating to the corresponding first action to the first device;
  maintaining, in the database, using the register, a third association between a second action associated with at least one of the plurality of customized automated applications and one or more of the plurality of customized automated applications; and
  causing based on the third association, using the manager, in response to performing the first action corresponding to the first defined input, the at least one of the customized automated applications identified to communicate information relating to the second action to the associated one or more of the plurality of customized automated applications via a communication channel defined by the third association.

23. A computer-implemented system operable to facilitate access to a plurality of customized automated application via a healthcare network, the healthcare network including a plurality of devices configured to process medical information, wherein, each of the plurality of customized automated applications is configured to be triggered, using a manager, in response to a defined input associated with each of the plurality of customized automated applications from a device from the plurality of devices and includes program code, configured to process medical information associated with the defined input received, the system including one or more processors, the one or more processors of the computer-implemented system being configured to:
  maintain, in a database, using a register, an association between a first customized automated application of the plurality of customized automated applications and at least one, different customized automated application, of the plurality of customized automated applications;
  trigger, using the manager, in response to receiving a defined input associated with the first customized automated application from a first device of the plurality of devices, the first customized automated application to process medical information associated with the defined input; and
  cause the first customized automated application to trigger, using the manager, the at least one of the plurality of customized automated applications and communicate information relating to the medical information processed by the first customized automated application;
  maintain, in the database, using the register, a second association between an action associated with at least one of the plurality of customized automated applications and one or more of the plurality of customized automated applications; and
  cause based on the second association, using the manager, in response to process medical information associated with the defined input, the at least one of the customized automated applications identified to communicate information relating to the action to the associated one or more of the plurality of customized automated applications via a communication channel defined by the second association.

* * * * *